United States Patent [19]

Blythin

[11] Patent Number: 4,569,936
[45] Date of Patent: Feb. 11, 1986

[54] ANTI-INFLAMMATORY SUBSTITUTED 9H-8-OXO-PYRIMIDO[2,1-F]PURINE-2,4-DIONES

[75] Inventor: David J. Blythin, North Caldwell, N.J.

[73] Assignee: Schering Corporation, Madison, N.J.

[21] Appl. No.: 544,320

[22] Filed: Oct. 21, 1983

Related U.S. Application Data

[63] Continuation-in-part of Ser. No. 436,247, Oct. 25, 1982, abandoned.

[51] Int. Cl.$^4$ .............................................. A61K 31/52
[52] U.S. Cl. .................................... 514/267; 544/251
[58] Field of Search ........................ 544/251; 424/253

[56] References Cited

U.S. PATENT DOCUMENTS

| | | | |
|---|---|---|---|
| 3,637,684 | 1/1972 | Goldman | 544/251 X |
| 3,770,741 | 11/1973 | Goldman | 544/251 |
| 4,228,164 | 10/1980 | Szebeni et al. | 424/246 |

FOREIGN PATENT DOCUMENTS 1226575  3/1971  United Kingdom .

*Primary Examiner*—Donald G. Daus
*Assistant Examiner*—Diana G. Rivers
*Attorney, Agent, or Firm*—Stephen I. Miller

[57] ABSTRACT

Substituted 9H-8-oxo-pyrimido[2,1-f]purine-2,4-diones their tautomers and salts are anti-inflammatory agents. Methods for their preparation and use are described.

18 Claims, No Drawings

ANTI-INFLAMMATORY SUBSTITUTED 9H-8-OXO-PYRIMIDO[2,1-f]PURINE-2,4-DIONES

CROSS REFERENCE TO RELATED APPLICATION

This application is a continuation-in-part of abandoned U.S. application Ser. No. 436,247 filed Oct. 25, 1982 now abandoned.

The present invention relates to substituted 9H-8-oxo-pyrimido[2,1-f]purine-2,4-diones and tautomers thereof. These compounds are useful as anti-inflammatory agents for treating inflammatory conditions such as arthritis, spondylitis, and tendonitis in mammals.

In a composition of matter aspect, the invention relates to compounds having the structural formula I

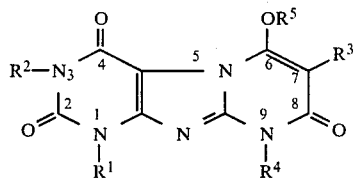

wherein
$R^1$ and $R^2$ are independently selected from hydrogen, cycloalkyl having from 3 to 8 carbon atoms, alkenyl having from 3 to 8 carbon atoms, alkynyl having from 3 to 8 carbon atoms, phenyl, substituted phenyl, alkyl having from 1 to 6 carbon atoms [which may be substituted with cycloalkyl having from 3 to 8 carbon atoms, phenyl, quinolinyl, isoquinolinyl, pyridyl, thiazolyl, 1,3,4-thiadiazolyl, thienyl and substituted phenyl, quinolinyl, isoquinolinyl, pyridyl, thiazolyl, 1,3,4-thiadiazolyl, thienyl];

$R^3$ is hydrogen, formyl, cycloalkyl having from 3 to 8 carbon atoms, alkenyl having from 2 to 8 carbon atoms, alkynyl having from 3 to 8 carbon atoms, cycloalkenyl having from 5 to 8 carbon atoms, acyloxyalkyl having from 2 to 12 carbon atoms, —alkyl—X—$C_pH_{2p+1}$ (wherein the alkyl portion has 1 to 6 carbon atoms, p is an integer from 0 to 4, and X represents CO, O, S, $S^+$—$O^-$, $SO_2$ or —$NC_rH_{2r+1}$ wherein r is an integer from 0 to 4), —$(CH_2)_n CONR^6R^7$ (wherein $R^6$ and $R^7$ are independently hydrogen or alkyl having from 1 to 6 carbon atoms, and n is an integer from 0 to 6), —$(CH_2)_m C(O)OR^8$ (wherein $R^8$ is hydrogen, alkyl having from 1 to 6 carbon atoms or a pharmaceutically acceptable metal or amine cation and m is an integer from 0 to 6), phenyl, substituted phenyl, alkyl having from 1 to 6 carbon atoms [which may be substituted with hydroxy, sulfhydryl, cyano, amino, halo, cycloalkyl having from 3 to 8 carbon atoms, phenyl, quinolinyl, isoquinolinyl, pyridyl, thiazolyl, 1,3,4-thiadiazolyl, thienyl and substituted phenyl, quinolinyl, isoquinolinyl, pyridyl, thiazolyl, 1,3,4thiadiazolyl and thienyl];

$R^4$ is hydrogen, phenyl, quinolinyl, isoquinolinyl, pyridyl, thiazolyl, 1,3,4-thiadiazolyl, thienyl, and substituted phenyl, quinolinyl, isoquinolinyl, pyridyl, thiazolyl, 1,3,4-thiadiazolyl and thienyl, alkyl having from 1 to 6 carbon atoms [which may be substituted with cycloalkyl having from 3 to 8 carbon atoms, phenyl, quinolinyl, isoquinolinyl, pyridyl, thiazolyl, 1,3,4-thiadiazolyl, thienyl and substituted phenyl, quinolinyl, isoquinolinyl, pyridyl, thiazolyl, 1,3,4-thiadiazolyl and thienyl];

$R^5$ is hydrogen, alkyl having from 1 to 4 carbon atoms,

(wherein $R^9$ is alkyl having from 1 to 6 carbon atoms), or a pharmaceutically acceptable metal or amine cation.

Preferred embodiments of the present invention relate to compounds having the structural formula I and the pharmaceutically acceptable salts thereof, wherein $R^1$ and $R^2$ are independently selected from alkyl of 1 to 4 carbon atoms;

$R^3$ is alkenyl having from 2 to 8 carbon atoms, alkynyl having from 3 to 8 carbon atoms, cycloalkenyl having from 5 to 8 carbon atoms, —alkyl—X—$C_pH_{2p+1}$ (wherein the alkyl portion has 1 to 6 carbon atoms, p is an integer from 0 to 4, and X represents O, S, $S^+O^-$, $SO_2$ or —$NC_rH_{2r+1}$ (wherein r is an integer from 0 to 4)), —$(CH_2)_n C(O)$—$NR^6R^7$ (wherein $R^6$ and $R^7$ are independently hydrogen or alkyl having from 1 to 6 carbon atoms, and n is an integer from 0 to 6), —$(CH_2)_m C(O)OR^8$ (wherein $R^8$ is alkyl having from 1 to 6 carbon atoms and m is an integer from 0 to 6), alkyl having from 1 to 6 carbon atoms which may be substituted with hydroxy or sulfhydryl; $R^4$ is alkyl having from 1 to 6 carbon atoms which is substituted with either phenyl or substituted phenyl; $R^5$ is hydrogen or a pharmaceutically acceptable cation.

More preferred values for $R^1$ and $R^2$ are alkyl of 1 to 3 carbon atoms. Most preferably $R^1$ and $R^2$ are methyl.

More preferred values for $R^3$ are alkenyl having from 3 to 8 carbon atoms, alkynyl having from 3 to 8 carbon atoms and alkyl having from 1 to 6 carbon atoms. Most preferably $R^3$ is n-propyl, n-butyl, propargyl (—$CH_2C \equiv CH$), allyl or prenyl (—$CH_2CH = C(CH_3)_2$).

More preferred values for $R^4$ are —$CH_2$—phenyl and —$CH_2$—substituted phenyl. Most preferably $R^4$ is benzyl or p-fluorobenzyl.

More preferred values for $R^5$ are hydrogen or a pharmaceutically acceptable metal cation, most preferably the sodium cation.

The preferred species having structural formula I are as follows:
9-(4-Fluorobenzyl)-1,3-dimethyl-6-hydroxy-7-(2-propynyl)-pyrimido-[2,1-f]purine-2,4,8-(1H,3H,9H)-trione;
9-Benzyl-1,3-dimethyl-6-hydroxy-7-(3-methyl-2-butenyl)-pyrimido-[2,1-f]purine-2,4,8(1H,3H,9H)-trione;
9-Benzyl-1,3-dimethyl-6-hydroxy-7-(2-propynyl)-pyrimido-[2,1-f]purine-2,4,8(1H,3H,9H)-trione;
9-(4-Fluorobenzyl)-6-hydroxy-1,3-dimethyl-7-n-propyl-9H-8-oxo-pyrimido[2,1-f]purine-2,4-dione;
9-(4-Fluorobenzyl)-1,3-dimethyl-6-hydroxy-7-(n-butyl)-9H-8-oxopyrimido[2,1-f]purine-3,4-dione;
9-Benzyl-1,3-dimethyl-8-hydroxy-7-(n-butyl)-9H-6-oxo-pyrimido[2,1-f]purine-2,4-dione;
9-Benzyl-1,3-dimethyl-8-hydroxy-7-n-propyl-9H-6-oxo-pyrimido[2,3-f]purine-2,4-dione; and
1,3-Dimethyl-9-(4-fluorobenzyl)-6-hydroxy-7-(3-methyl-2-butenyl)-pyrimido[2,1-f]purine-2,4,8(1H,3H,9H)-trione.

The above species are also preferred in the form of their sodium salts.

When utilized herein and in the appended claims the below listed terms, unless specified otherwise, are defined as follows:

halogen: fluorine, chlorine, bromine and iodine;
alkyl having from 1 to 6 carbon atoms: straight and branched carbon chains;
substituted phenyl, quinolinyl, isoquinolinyl, pyridyl, thiazolyl, 1,3,4-thiadiazolyl, thienyl: phenyl, quinolinyl, isoquinolinyl, pyridyl, thiazolyl, 1,3,4-thiaziazolyl and thienyl substituted with 1 to 3 substituents independently selected from halogen, trifluoromethyl, nitro, cyano, phenyl,

—CO$_2$H, hydroxy, —S(O)$_a$R$^{10}$ (wherein R$^{10}$ is alkyl having from 1 to 6 carbon atoms and a is 0, 1 or 2), —OR$^{11}$ (wherein R$^{11}$ is alkyl having from 1 to 6 carbon atoms, alkenyl having from 3 to 8 carbon atoms, alkynyl having from 3 to 8 carbon atoms, phenyl, benzyl, or

(wherein R$^{12}$ is alkyl having from 1 to 6 carbon atoms alkoxy having from 1 to 6 carbon atoms)), alkyl having from 1 to 6 carbon atoms which may be substituted with hydroxy, cyano and

(wherein R$^{13}$ is hydrogen or alkyl having from 1 to 4 carbon atoms).

pharmaceutically acceptable metal and amine cations—lithium, sodium, potassium, magnesium, calcium, aluminum, zinc, iron, copper, gold, ammonium, methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, alpha-phenylethylamine, beta-phenylethylamine, ethylenediamine, diethylenetriamine, piperidine, morpholine, pyrrolidine, piperazine, 1-methylpiperidine, N-ethylmorpholine, 1-isopropylpyrrolidine, 2-methylpyrrolidine, 1,4-dimethylpiperazine, 2-methylpiperidine, mono-, di- and triethanolamine, ethyldiethanolamine, n-butylethanolamine, 2-amino-1-butanol, 2-amino-2-ethyl-1,3-propanediol, 2-amino-2-methyl-1-propanol, tris(hydroxymethyl)aminomethane, lysine, N-phenylethanolamine, N-(p-tetramylphenyl)diethanolamine, galactamine, N-phenylglucamine, N-methylglucosamine and the like.

The following reaction scheme illustrates the preparation of many of the compounds of the present invention:

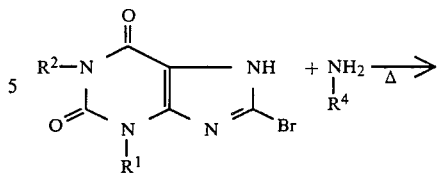

II

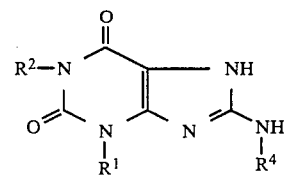

III

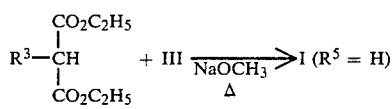

wherein R$^1$, R$^2$, R$^3$ and R$^4$ are as defined above.

The final compounds of the invention having structural formula I wherein R$^5$=H may be prepared by reacting a correspondingly substituted compound having structural formula III with a suitably substituted dialkylmalonate in the presence of a stoichiometric amount of a base, b, such as sodium hydride at an elevated temperature substantially as described in example 3 hereinbelow.

Alternatively, the compounds of this invention wherein R$^3$=R$^5$=H may be prepared by reacting a correspondingly substituted compound having structural formula III with ethyl malonyl chloride as described in example 9 hereinbelow.

Compounds having the structural formula I wherein R$^3$=H and R$^5$=H or a sodium cation may be alkylated as shown in the reaction scheme below:

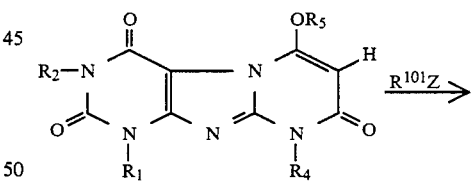

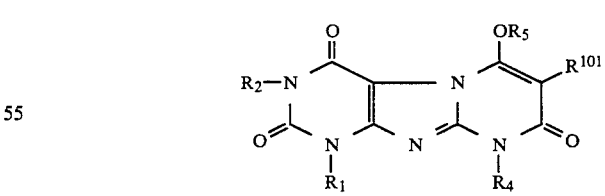

wherein R$^1$, R$^2$, R$^4$ are as defined above and Z is a halogen. This process is best suited for activated electrophiles, e.g. such R$^{101}$ groups as 3-halo alkenes, 3-halo alkynes α-halo esters, benzyl halides, α-halo acetonitriles and the equivalents of these groups which are known in the art. A crown ether (e.g. 18-crown-6) may be added in order to improve the yield.

R$^5$ alkyl derivatives may be conveniently prepared by a diazoalkane reaction whereas the carboxylic acyl group may be introduced by use of the corresponding acid chloride or by other art recognized procedures.

The intermediates of formula III may be prepared from readily available starting materials according to the sequence of steps described below.

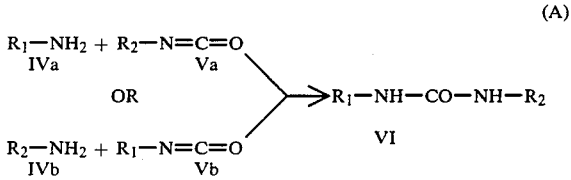
(A)

The ureas of formula VI may be prepared by reacting approximately equimolar quantities of an amine ($R_1$—$NH_2$ or $R_2$—$NH_2$) with an isocyanate ($R_2$—N=C=O or $R_1$—N=C=O) in an inert solvent, e.g., chloroform.

$$R_1-NH-CO-NH-R_2 + \overset{CN}{\underset{}{CH_2}}-CO_2H \xrightarrow[AcOH]{Ac_2O}$$ (B)

VI

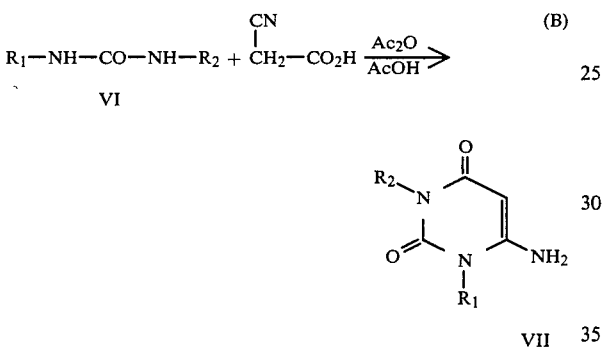
VII

Compounds of formula VII may be prepared by the well known Traube purine synthesis or a modification thereof. Equimolar quantities of the compound of formula VI and cyanoacetic acid are heated to 60° C. with two equivalents of acetic anhydride using glacial acetic acid as solvent. After 2 to 8 hours as much as possible of the acetic acid and acetic anhydride are removed at 60° C. in vacuo. The resultant mixture is poured into water and made basic, e.g., with solid sodium carbonate. The mixture is boiled 1–4 hours, then cooled. On standing either a solid will form which may be filtered off and purified, or an oil will form which may be extracted and purified.

Note that for compounds of formula VI where $R_1$ and $R_2$ are different, two different compounds of formula VII may be formed, i.e.,

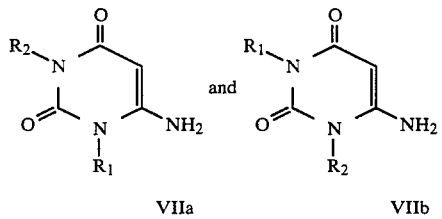

These compounds may be separated by fractional crystallization or by chromatography (e.g. column or HPLC).

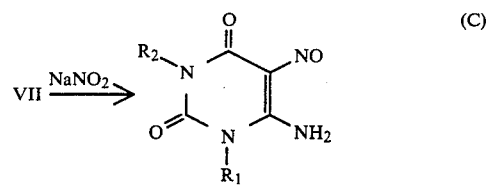
VIII

The purified 6-aminouracil compounds of formula VII may be converted to the 5-nitroso-6-aminouracil compounds of formula VIII by combining the 6-aminouracil derivative and sodium nitrite (one equivalent) and boiling in ethanol/water while adding glacial acetic acid. The nitroso compound of formula VIII which precipitates is then filtered off, washed with water and dried.

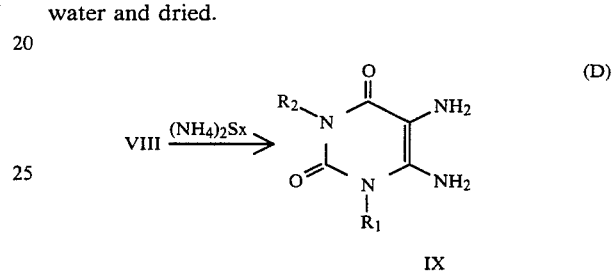
IX

The 6-amino-5-nitrosouracil compound of formula VIII is reduced to the corresponding 5-amino-compound of formula IX in aqueous suspension by the use of an excess of ammonium polysulfide solution with warming. When the color is discharged, the mixture is cooled and the supernatant liquid is decanted off. The residue is dissolved in methylene chloride, which is dried and evaporated. The crude product is used in the next step.

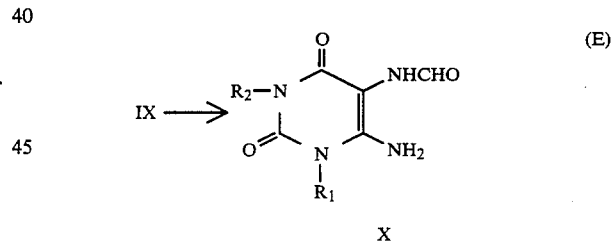
X

The 5,6-diaminouracil compound of formula IX is heated with excess formic acid at 120°–150° C. for 1–4 hours, then allowed to stand at room temperature overnight. Most of the acid is then removed (75° C.; reduced pressure) and the residue is dissolved in hot methanol and filtered. The product of formula X is isolated by chilling and filtering off the resulting solid or by evaporation of the methanol.

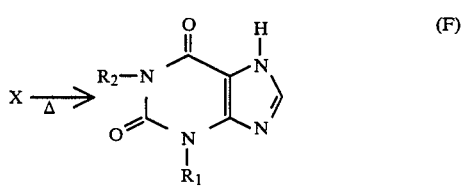
XI

The 6-amino-5-formamidouracil compound of formula X is heated to 250°–285° C. until frothing ceases (10–60 mins.). The product is then cooled and the crude product of formula XI is recrystallized, e.g. from MeOH/H$_2$O.

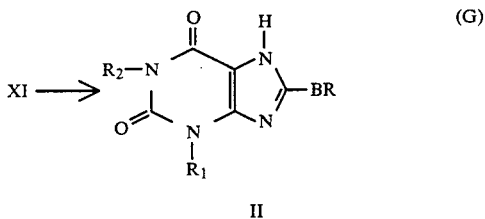

The xanthine compound of formula XI is dissolved in glacial acetic acid. The solution is warmed gradually to 100° C. while a solution of bromine in acetic acid is slowly added until thin layer chromatography shows that starting material has been consumed. The product, a compound of formula II, is isolated by pouring the reaction mixture into water, filtering and recrystallizing, if necessary.

The 8-bromoxanthine of formula II is converted to the 8-substituted-amino-xanthine of formula III by heating with excess amine at elevated temperatures as described in Example 1, below.

Compounds of the formula I wherein R$^5$ is hydrogen may exist in tautomeric forms.

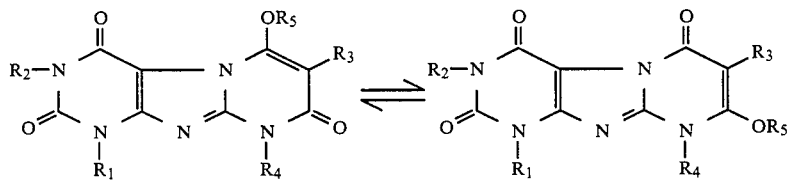

Such tautomeric forms are equivalent for purposes of the invention.

The following examples further illustrate the preparation of the compounds of the present invention:

EXAMPLE 1

8-Benzylamino-1,3-di-n-butyl-xanthine

Heat together a mixture of one equivalent of 8-bromo-1,3-di-n-butyl-xanthine with three to four equivalents of benzylamine at 160°–180° C. until thin layer chromatography analysis shows that no starting xanthine remains. Cool. Triturate with ethanol and water to yield 8-benzylamino-1,3-di-n-butyl-xanthine.

Similarly, prepare other 8-(substituted amino)-1,3-disubstituted xanthines required for the preparation of the compounds of the present invention from the corresponding 8-bromo-(or 8-chloro)-1,3-disubstituted xanthines by heating with excess amine at elevated temperatures, in a sealed vessel, if necessary.

EXAMPLE 2

9-Benzyl-1,3-dimethyl-6-Hydroxy-7-n-propyl-9H-8-oxo-pyrimido[2,1-f]purine-2,4-dione (or tautomer)

Suspend 8-benzylamino-theophylline (10 g) in diethyl n-propyl malonate (65 ml). Add sodium methoxide (0.7 g), and stir and heat to about 200° C. (bath temperature). Separate the ethanol which is formed with a Dean and Stark trap. After about 4 to 6 hours, raise the bath temperature to about 215° C. until no more starting material is present (as shown by thin layer chromatography).

Cool to below 60° C. and add ethanol. Stir and triturate and then filter, wash and air dry. Recrystallize the product from acetonitrile (about 60 parts). Wash with ether and dry in vacuo at 70° to 75° C. to yield the title compound having a melting point of 217° C. (yield about 62%).

Similarly, prepare the following:

9-Benzyl-1,3,7-trimethyl-6-hydroxy-9H-8-oxo-pyrimido[2,1-f]purine-2,4-dione, m.p. 204° C.;
9-Benzyl-1,3-dimethyl-7-n-butyl-6-hydroxy-9H-8-oxo-pyrimido[2,1-f]purine-2,4-dione, m.p. 162° C.;
9-Benzyl-1,3-dimethyl-7-iso-butyl-6-hydroxy-9H-8-oxo-pyrimido[2,1-f]purine-2,4-dione, m.p. 168° C.;
9-Phenyl-1,3,7-trimethyl-6-hydroxy-9H-8-oxo-pyrimido[2,1-f]purine-2,4-dione, m.p. >260° C.;
9-Phenyl-1,3-dimethyl-7-n-propyl-6-hydroxy-9H-8-oxo-pyrimido[2,1-f]purine-2,4-dione, m.p. >260° C.;
9-Phenyl-1,3-dimethyl-7-n-butyl-6-hydroxy-9H-8-oxo-pyrimido[2,1-f]purine-2,4-dione, m.p. 227° C.;
9-Phenyl-1,3-dimethyl-7-iso-butyl-6-hydroxy-9H-8-oxo-pyrimido[2,1-f]purine-2,4-dione, m.p. >260° C.;
9-Phenyl-1,3-dimethyl-7-n-pentyl-6-hydroxy-9H-8-oxo-pyrimido[2,1-f]purine-2,4-dione, m.p. 219° C.;
9-(p-Fluorobenzyl)-1,3,7-trimethyl-6-hydroxy-9H-8-oxo-pyrimido[2,1-f]purine-2,4-dione, m.p. 248° C. (sinters);
9-(p-Fluorobenzyl)-1,3-dimethyl-7-n-propyl-6-hydroxy-9H-8-oxo-pyrimido[2,1-f]purine-2,4-dione, m.p. 215° C.;
9-(p-Chlorobenzyl)-1,3-dimethyl-7-n-propyl-6-hydroxy-9H-8-oxo-pyrimido[2,1-f]purine-2,4-dione, m.p. 195° C.;
9-(p-Fluorophenyl)-1,3-dimethyl-7-n-propyl-6-hydroxy-9H-8-oxo-pyrimido[2,1-f]purine-2,4-dione, m.p. >260° C.;
9-(p-Fluorophenyl)-1,3-dimethyl-7-n-butyl-6-hydroxy-9H-8-oxo-pyrimido[2,1-f]purine-2,4-dione, m.p. >260° C.;
9-(2-Pyridylmethyl)-1,3-dimethyl-7-n-propyl-6-hydroxy-9H-8-oxo-pyrimido[2,1-f]purine-2,4-dione, m.p. 208° C.;
9-(2-Pyridylmethyl)-1,3-dimethyl-7-benzyl-6-hydroxy-9H-8-oxo-pyrimido[2,1-f]purine-2,4-dione, m.p. 199° C.;
9-Benzyl-1,3-di-n-butyl-7-methyl-6-hydroxy-9H-8-oxo-pyrimido[2,1-f]purine-2,4-dione, m.p. 138° C.;
1,3-Dimethyl-9-benzyl-6-hydroxy-9H-8-oxopyrimido[2,1-f]-purine-2,4-dione, m.p. 209°–222° C.;
1,3-Dimethyl-9-cyclohexylmethyl-6-hydroxy-7-n-butyl-9H-8-oxo-pyrimido[2,1-f]purine-2,4-dione, m.p. 151°–153° C.;

Also, similarly prepare the following:

9-Benzyl-1,3-dimethyl-7-ethyl-6-hydroxy-9H-8-oxo-pyrimido[2,1-f]purine-2,4-dione;

9-Benzyl-1,3-dimethyl-7-n-pentyl-6-hydroxy-9H-8-oxo-pyrimido[2,1-f]purine-2,4-dione;
9-Benzyl-1,3-dimethyl-7-iso-pentyl-6-hydroxy-9H-8-oxo-pyrimido[2,1-f]purine-2,4-dione;
9-Benzyl-1,3-dimethyl-7-n-hexyl-6-hydroxy-9H-8-oxo-pyrimido[2,1-f]purine-2,4-dione;
9-Benzyl-1,3-dimethyl-7-n-heptyl-6-hydroxy-9H-8-oxo-pyrimido[2,1-f]purine-2,4-dione;
9-Benzyl-1,3-dimethyl-7-n-octyl-6-hydroxy-9H-8-oxo-pyrimido[2,1-f]purine-2,4-dione;
9-Benzyl-1,3-dimethyl-7-phenyl-6-hydroxy-9H-8-oxo-pyrimido[2,1-f]purine-2,4-dione;
7,9-Dibenzyl-1,3-dimethyl-6-hydroxy-9H-8-oxo-pyrimido[2,1-f]purine-2,4-dione;
9-Benzyl-1,3-dimethyl-7-(2-phenethyl)-6-hydroxy-9H-8-oxo-pyrimido[2,1-f]purine-2,4-dione;
9-Benzyl-1,3-dimethyl-7-iso-propyl-6-hydroxy-9H-8-oxo-pyrimido[2,1-f]purine-2,4-dione; m.p. 167°–168.5° C.
9-Benzyl-1,3-dimethyl-7-sec-butyl-6-hydroxy-9H-8-oxo-pyrimido[2,1-f]purine-2,4-dione;
9-Phenyl-1,3-dimethyl-7-ethyl-6-hydroxy-9H-8-oxo-pyrimido[2,1-f]purine-2,4-dione;
9-Phenyl-1,3-dimethyl-7-n-hexyl-6-hydroxy-9H-8-oxo-pyrimido[2,1-f]purine-2,4-dione;
9-Phenyl-1,3-dimethyl-7-n-heptyl-6-hydroxy-9H-8-oxo-pyrimido[2,1-f]purine-2,4-dione;
9-Phenyl-1,3-dimethyl-7-n-octyl-6-hydroxy-9H-8-oxo-pyrimido[2,1-f]purine-2,4-dione;
9-(p-Fluorobenzyl)-1,3-dimethyl-7-ethyl-6-hydroxy-9H-8-oxo-pyrimido[2,1-f]purine-2,4-dione;
9-(p-Fluorobenzyl)-1,3-dimethyl-7-iso-propyl-6-hydroxy-9H-8-oxo-pyrimido[2,1-f]purine-2,4-dione;
9-(p-Fluorobenzyl)-1,3-dimethyl-7-n-butyl-6-hydroxy-9H-8-oxo-pyrimido[2,1-f]purine-2,4-dione; m.p. 184.5°–186.5° C.
9-(p-Fluorobenzyl)-1,3-dimethyl-7-iso-butyl-6-hydroxy-9H-8-oxo-pyrimido[2,1-f]purine-2,4-dione;
9-(p-Fluorobenzyl)-1,3-dimethyl-7-sec-butyl-6-hydroxy-9H-8-oxo-pyrimido[2,1-f]purine-2,4-dione;
9-(p-Fluorobenzyl)-1,3-dimethyl-7-n-pentyl-6-hydroxy-9H-8-oxo-pyrimido[2,1-f]purine-2,4-dione;
9-(p-Fluorobenzyl)-1,3-dimethyl-7-iso-pentyl-6-hydroxy-9H-8-oxo-pyrimido[2,1-f]purine-2,4-dione;
9-(p-Fluorobenzyl)-1,3-dimethyl-7-n-hexyl-6-hydroxy-9H-8-oxo-pyrimido[2,1-f]purine-2,4-dione;
9-(p-Fluorobenzyl)-1,3-dimethyl-7-phenyl-6-hydroxy-9H-8-oxo-pyrimido[2,1-f]purine-2,4-dione; m.p. 228°–229° C.
9-(p-Fluorobenzyl)-1,3-dimethyl-7-benzyl-6-hydroxy-9H-8-oxo-pyrimido[2,1-f]purine-2,4-dione; m.p. 247°–248.5° C.
9-(p-Fluorobenzyl)-1,3-dimethyl-7-(2-phenethyl)-6-hydroxy-9H-8-oxo-pyrimido[2,1-f]purine-2,4-dione;
9-(p-Chlorobenzyl)-1,3,7-trimethyl-6-hydroxy-9H-8-oxo-pyrimido[2,1-f]purine-2,4-dione;
9-(p-Chlorobenzyl)-1,3-dimethyl-7-ethyl-6-hydroxy-9H-8-oxo-pyrimido[2,1-f]purine-2,4-dione;
9-(p-Chlorobenzyl)-1,3-dimethyl-7-iso-propyl-6-hydroxy-9H-8-oxo-pyrimido[2,1-f]purine-2,4-dione;
9-(p-Chlorobenzyl)-1,3-dimethyl-7-n-butyl-6-hydroxy-9H-8-oxo-pyrimido[2,1-f]purine-2,4-dione; m.p. 178° C.
9-(p-Chlorobenzyl)-1,3-dimethyl-7-iso-butyl-6-hydroxy-9H-8-oxo-pyrimido[2,1-f]purine-2,4-dione;
9-(p-Chlorobenzyl)-1,3-dimethyl-7-sec-butyl-6-hydroxy-9H-8-oxo-pyrimido[2,1-f]purine-2,4-dione;
9-(p-Chlorobenzyl)-1,3-dimethyl-7-n-pentyl-6-hydroxy-9H-8-oxo-pyrimido[2,1-f]purine-2,4-dione;
9-(p-Chlorobenzyl)-1,3-dimethyl-7-iso-pentyl-6-hydroxy-9H-8-oxo-pyrimido[2,1-f]purine-2,4-dione;
9-(p-Chlorobenzyl)-1,3-dimethyl-7-n-hexyl-6-hydroxy-9H-8-oxo-pyrimido[2,1-f]purine-2,4-dione;
9-(p-Fluorophenyl)-1,3,7-trimethyl-6-hydroxy-9H-8-oxo-pyrimido[2,1-f]purine-2,4-dione;
9-(p-Fluorophenyl)-1,3-dimethyl-7-ethyl-6-hydroxy-9H-8-oxo-pyrimido[2,1-f]purine-2,4-dione;
9-(p-Fluorophenyl)-1,3-dimethyl-7-iso-propyl-6-hydroxy-9H-8-oxo-pyrimido[2,1-f]purine-2,4-dione;
9-(p-Fluorophenyl)-1,3-dimethyl-7-iso-butyl-6-hydroxy-9H-8-oxo-pyrimido[2,1-f]purine-2,4-dione;
9-(p-Fluorophenyl)-1,3-dimethyl-7-n-pentyl-6-hydroxy-9H-8-oxo-pyrimido[2,1-f]purine-2,4-dione;
9-(p-Fluorophenyl)-1,3-dimethyl-7-n-hexyl-6-hydroxy-9H-8-oxo-pyrimido[2,1-f]purine-2,4-dione;
9-(p-Fluorophenyl)-1,3-dimethyl-7-phenyl-6-hydroxy-9H-8-oxo-pyrimido[2,1-f]purine-2,4-dione;
9-(p-Fluorophenyl)-1,3-dimethyl-7-benzyl-6-hydroxy-9H-8-oxo-pyrimido[2,1-f]purine-2,4-dione;
9-(m-Trifluoromethylbenzyl)-1,3,7-trimethyl-6-hydroxy-9H-8-oxo-pyrimido[2,1-f]purine-2,4-dione;
9-(m-Trifluoromethylbenzyl)-1,3-dimethyl-7-n-propyl-6-hydroxy-9H-8-oxo-pyrimido[2,1-f]purine-2,4-dione;
9-(m-Trifluoromethylbenzyl)-1,3-dimethyl-7L-n-butyl-6-hydroxy-9H-8-oxo-pyrimido[2,1-f]purine-2,4-dione;
9-(m-Trifluoromethylbenzyl)-1,3-dimethyl-7-iso-butyl-6-hydroxy-9H-8-oxo-pyrimido[2,1-f]purine-2,4-dione;
9-(m-Trifluoromethylbenzyl)-1,3-dimethyl-7-n-pentyl-6-hydroxy-9H-8-oxo-pyrimidol[2,1-f]purined-2,4-done;
9-(p-Methoxybenzyl)-1,3,7-trimethyl-6-hydroxy-9H-8-oxo-pyrimido[2,1-f]purine-2,4-dione;
9-(p-Methoxybenzyl)-1,3-dimethyl-7-n-propyl-6-hydroxy-9H-8-oxo-pyrimido[2,1-f]purine-2,4-dione; m.p. 207°–208° C.
9-(p-Methoxybenzyl)-1,3-dimethyl-7-n-butyl-6-hydroxy-9H-8-oxo-pyrimido[2,1-f]purine-2,4-dione;
9-(p-Methoxybenzyl)-1,3-dimethyl-7-n-pentyl-6-hydroxy-9H-8-oxo-pyrimido[2,1-f]purine-2,4-dione;
9-(2-Pyridylmethyl)-1,3,7-trimethyl-6-hydroxy-9H-8-oxo-pyrimido[2,1-f]purine-2,4-dione;
9-(2-Pyridylmethyl)-1,3-dimethyl-7-n-butyl-6-hydroxy-9H-8-oxo-pyrimido[2,1-f]purine-2,4-dione;
9-(2-Pyridylmethyl)-1,3-dimethyl-7-n-pentyl-6-hydroxy-9H-8-oxo-pyrimido[2,1-f]purine-2,4-dione;
9-(2-Pyridylmethyl)-1,3-dimethyl-7-phenyl-6-hydroxy-9H-8-oxo-pyrimido[2,1-f]purine-2,4-dione;
9-(n-butyl)-1,3,7-trimethyl-6-hydroxy-9H-8-oxo-pyrimido[2,1-f]purine-2,4-dione;
9-(n-butyl)-1,3-dimethyl-7-n-propyl-6-hydroxy-9H-8-oxo-pyrimido[2,1-f]purine-2,4-dione;
9-(n-butyl)-1,3-dimethyl-7-iso-butyl-6-hydroxy-9H-8-oxo-pyrimido[2,1-f]pyrine-2,4-dione;
9-(n-butyl)-1,3-dimethyl-7-phenyl-6-hydroxy-9H-8-oxo-pyrimido[2,1-f]purine-2,4-dione;
9-(n-butyl)-1,3-dimethyl-7-benzyl-6-hydroxy-9H-8-oxo-pyrimido[2,1-f]purine-2,4-dione;
9-(n-butyl)-1,3-dimethyl-7-(p-fluorobenzyl)-6-hydroxy-9H-8-oxo-pyrimido[2,1-f]purine-2,4-dione;
9-(2-Thiophenemethyl)-1,3,7-trimethyl-6-hydroxy-9H-8-oxo-pyrimido[2,1-f]purine-2,4-dione;
9-(2-Thiophenemethyl)-1,3-dimethyl-7-ethyl-6-hydroxy-9H-8-oxo-pyrimido[2,1-f]purine-2,4-dione;

9-(2-Thiophenemethyl)-1,3-dimethyl-7-n-propyl-6-hydroxy-9H-8-oxo-pyrimido[2,1-f]purine-2,4-dione; m.p. 225°–226° C.
9-(2-Thiophenemethyl)-1,3-dimethyl-7-n-butyl-6-hydroxy-9H-8-oxo-pyrimido[2,1-f]purine-2,4-dione;
9-(2-Thiophenemethyl)-1,3-dimethyl-7-iso-butyl-6-hydroxy-9H-8-oxo-pyrimido[2,1-f]purine-2,4-dione;
9-(2-Thiophenemethyl)-1,3-dimethyl-7-n-pentyl-6-hydroxy-9H-8-oxo-pyrimido[2,1-f]purine-2,4-dione;
9-(2-Thiophenemethyl)-1,3-dimethyl-7-n-hexyl-6-hydroxy-9H-8-oxo-pyrimido[2,1-f]purine-2,4-dione;
9-(2-Thiophenemethyl)-1,3-dimethyl-7-phenyl-6-hydroxy-9H-8-oxo-pyrimido[2,1-f]purine-2,4-dione;
9-(2-Thiophenemethyl)-1,3-dimethyl-7-benzyl-6-hydroxy-9H-8-oxo-pyrimido[2,1-f]purine-2,4-dione;
9-(4-Methylthiophenyl)-1,3,7-trimethyl-6-hydroxy-9H-8-oxo-pyrimido[2,1-f]purine-2,4-dione;
9(4-Methylthiophenyl)-1,3-dimethyl-7-n-propyl-6-hydroxy-9H-8-oxo-pyrimido[2,1-f]purine-2,4-dione;
9-(4-Methylthiophenyl)-1,3-dimethyl-7-n-butyl-6-hydroxy-9H-8-oxo-pyrimido[2,1-f]purine-2,4-dione;
9-(4-Methylthiophenyl)-1,3-dimethyl-7-iso-butyl-6-hydroxy-9H-8-oxo-pyrimido[2,1-f]purine-2,4-dione;
9-(4-Methylthiophenyl)-1,3-dimethyl-7-n-pentyl-6-hydroxy-9H-8-oxo-pyrimido[2,1-f]purine-2,4-dione;
9-(4-Methylthiophenyl)-1,3-dimethyl-7-phenyl-6-hydroxy-9H-8-oxo-pyrimido[2,1-f]purine-2,4-dione;
9-(4-Methylthiophenyl)-1,3-dimethyl-7-benzyl-6-hydroxy-9H-8-oxo-pyrimido[2,1-f]purine-2,4-dione;
9-Benzyl-1,3-diethyl-7-methyl-6-hydroxy-9H-8-oxo-pyrimido[2,1-f]purine-2,4-dione;
9-Benzyl-1,3-diethyl-7-n-propyl-6-hydroxy-9H-8-oxo-pyrimido[2,1-f]purine-2,4-dione;
9-Benzyl-1,3-diethyl-7-n-butyl-6-hydroxy-9H-8-oxo-pyrimido[2,1-f]purine-2,4-dione;
9-Benzyl-1,3-diethyl-7-iso-butyl-6-hydroxy-9H-8-oxo-pyrimido[2,1-f]purine-2,4-dione;
9-Benzyl-1,3-diethyl-7-n-pentyl-6-hydroxy-9H-8-oxo-pyrimido[2,1-f]purine-2,4-dione;
9-Benzyl-1,3-diethyl-7-iso-pentyl-6-hydroxy-9H-8-oxo-pyrimido[2,1-f]purine-2,4-dione;
9-Benzyl-1,3-diethyl-7-n-hexyl-6-hydroxy-9H-8-oxo-pyrimido[2,1-f]purine-2,4-dione;
9-Benzyl-1,3-diethyl-7-phenyl-6-hydroxy-9H-8-oxo-pyrimido[2,1-f]purine-2,4-dione;
9-Phenyl-1,3-diethyl-7-methyl-6-hydroxy-9H-8-oxo-pyrimido[2,1-f]purine-2,4-dione;
9-Phenyl-1,3-diethyl-7-n-propyl-6-hydroxy-9H-8-oxo-pyrimido[2,1-f]purine-2,4-dione;
9-Phenyl-1,3-diethyl-7-iso-propyl-6-hydroxy-9H-8-oxo-pyrimido[2,1-f]purine-2,4-dione;
9-Phenyl-1,3-diethyl-7-n-butyl-6-hydroxy-9H-8-oxo-pyrimido[2,1-f]purine-2,4-dione;
9-Phenyl-1,3-diethyl-7-iso-butyl-6-hydroxy-9H-8-oxo-pyrimido[2,1-f]purine-2,4-dione;
9-Phenyl-1,3-diethyl-7-n-pentyl-6-hydroxy-9H-8-oxo-pyrimido[2,1-f]purine-2,4-dione;
9-Phenyl-1,3-diethyl-7-iso-pentyl-6-hydroxy-9H-8-oxo-pyrimido[2,1-f]purine-2,4-dione;
9-Phenyl-1,3-diethyl-7-n-hexyl-6-hydroxy-9H-8-oxo-pyrimido[2,1-f]purine-2,4-dione;
9-(p-Fluorobenzyl)-1,3-diethyl-7-methyl-6-hydroxy-9H-8-oxopyrimido[2,1-f]purine-2,4-dione;
9-(p-Fluorobenzyl)-1,3-diethyl-7-n-propyl-6-hydroxy-9H-8-oxopyrimido[2,1-f]purine-2,4-dione;
9-(p-Fluorobenzyl)-1,3-diethyl-7-n-butyl-6-hydroxy-9H-8-oxopyrimido[2,1-f]purine-2,4-dione;
9-(p-Fluorobenzyl)-1,3-diethyl-7-iso-butyl-6-hydroxy-9H-8-oxopyrimido[2,1-f]purine-2,4-dione;
9-(p-Fluorobenzyl)-1,3-diethyl-7-n-pentyl-6-hydroxy-9H-8-oxopyrimido[2,1-f]purine-2,4-dione;
9-(p-Chlorobenzyl)-1,3-diethyl-7-methyl-6-hydroxy-9H-8-oxopyrimido[2,1-f]purine-2,4-dione;
9-(p-Chlorobenzyl)-1,3-diethyl-6-hydroxy-9H-8-oxopyrimido[2,1-f]purine-2,4-dione;
9-(p-Chlorobenzyl)-1,3,7-triethyl-6-hydroxy-9H-8-oxopyrimido[2,1-f]purine-2,4-dione;
9-(p-Chlorobenzyl)-1,3-diethyl-7-n-propyl-6-hydroxy-9H-8-oxopyrimido[2,1-f]purine-2,4-dione;
9-(p-Chlorobenzyl)-1,3-diethyl-7-n-butyl-6-hydroxy-9H-8-oxopyrimido[2,1-f]purine-2,4-dione;
9-(p-Methoxybenzyl)-1,3-diethyl-7-methyl-6-hydroxy-9H-8-oxopyrimido[2,1-f]purine-2,4-dione;
9-(p-Methoxybenzyl)-1,3,7-triethyl-6-hydroxy-9H-8-oxo-pyrimido[2,1-f]purine-2,4-dione;
9-(p-Methoxybenzyl)-1,3-diethyl-7-n-propyl-6-hydroxy-9H-8-oxopyrimido[2,1-f]purine-2,4-dione;
9-(p-Methoxybenzyl)-1,3-diethyl-7-n-butyl-6-hydroxy-9H-8-oxopyrimido[2,1-f]purine-2,4-dione;
9-(p-Methoxybenzyl)-1,3-diethyl-7-n-hexyl-6-hydroxy-9H-8-oxopyrimido[2,1-f]purine-2,4-dione;
9-n-Butyl-1,3-diethyl-7-phenyl-6-hydroxy-9H-8-oxo-pyrimido[2,1-f]purine-2,4-dione;
9-n-Butyl-1,3-diethyl-7-benzyl-6-hydroxy-9H-8-oxo-pyrimido[2,1-f]purine-2,4-dione;
9-n-Butyl-1,3-diethyl-7-(2-phenethyl)-6-hydroxy-9H-8oxo-pyrimido[2,1-f]purine-2,4-dione;
9-n-Butyl-1,3-diethyl-7-(p-fluorobenzyl)-6-hydroxy-9H-8-oxopyrimido[2,1-f]purine-2,4-dione;
9-n-Butyl-1,3-diethyl-7-(p-chlorobenzyl)-6-hydroxy-9H-8-oxopyrimido[2,1-f]purine-2,4-dione;
9-n-Butyl-1,3-diethyl-7-(p-methoxybenzyl)-6-hydroxy-9H-8-oxopyrimido[2,1-f]purine-2,4-dione;
9-(3-Pyridylmethyl)-1,3-diethyl-7-methyl-6-hydroxy-9H-8-oxopyrimido[2,1-f]purine-2,4-dione;
9-(3-Pyridylmethyl)-1,3-diethyl-7-n-propyl-6-hydroxy-9H-8-oxopyrimido[2,1-f]purine-2,4-dione;
9-(3-Pyridylmethyl)-1,3-diethyl-7-n-butyl-6-hydroxy-9H-8-oxopyrimido[2,1-f]purine-2,4-dione;
9-(3-Pyridylmethyl)-1,3-diethyl-7-iso-butyl-6-hydroxy-9H-8-oxopyrimido[2,1-f]purine-2,4-dione;
9-(3-Pyridylmethyl)-1,3-diethyl-7-n-pentyl-6-hydroxy-9H-8-oxopyrimido[2,1-f]purine-2,4-dione;
9-Benzyl-1,3-di-n-propyl-7-methyl-6-hydroxy-9H-8-oxo-pyrimido[2,1-f]purine-2,4-dione;
9-Benzyl-1,3-di-n-propyl-7-ethyl-6-hydroxy-9H-8-oxopyrimido[2,1-f]purine-2,4-dione;
9-Benzyl-1,3,7-tri-n-propyl-6-hydroxy-9H-8-oxopyrimido[2,1f]purine-2,4-dione;
9-Benzyl-1,3-di-n-propyl-7-n-butyl-6-hydroxy-9H-8-oxo-pyrimido[2,1-f]purine-2,4-dione;
9-Benzyl-1,3-di-n-propyl-7-phenyl-6-hydroxy-9H-8-oxo-pyrimido[2,1-f]purine-2,4-dione;
9-(p-Fluorobenzyl)-1,3-di-n-propyl-7-methyl-6-hydroxy-9H-8-oxopyrimido[2,1-f]purine-2,4-dione;
9-(p-Fluorobenzyl)-1,3-di-n-propyl-7-ethyl-6-hydroxy-9H-8-oxopyrimido[2,1-f]purine-2,4-dione;
9-(p-Fluorobenzyl)-1,3,7-tri-n-propyl-6-hydroxy-9H-8-oxopyrimido[2,1-f]purine-2,4-dione;
9-(p-Fluorobenzyl)-1,3-di-n-propyl-7-n-butyl-6-hydroxy-9H-8-oxopyrimido[2,1-f]purine-2,4-dione;
9-(p-Fluorobenzyl)-1,3-di-n-propyl-7-iso-butyl-6-hydroxy-9H-8-oxopyrimido[2,1-f]purine-2,4-dione;
9-(p-Fluorobenzyl)-1,3-di-n-propyl-7-phenyl-6-hydroxy-9H-8-oxopyrimido[2,1-f]purine-2,4-dione;

9-(p-Fluorobenzyl)-1,3-di-n-propyl-7-benzyl-6-hydroxy-9H-8-oxopyrimido[2,1-f]purine-2,4-dione;
9-(p-Methoxybenzyl)-1,3-di-n-propyl-7-methyl-6-hydroxy-9H-8-oxopyrimido[2,1-f]purine-2,4-dione;
9-(p-Methoxybenzyl)-1,3-di-n-propyl-7-ethyl-6-hydroxy-9H-8-oxopyrimido[2,1-f]purine-2,4-dione;
9-(p-Methoxybenzyl)-1,3,7-tri-n-propyl-6-hydroxy-9H-8-oxopyrimido[2,1-f]purine-2,4-dione;
9-(p-Methoxybenzyl)-1,3-di-n-propyl-7-n-butyl-6-hydroxy-9H-8-oxopyrimido[2,1-f]purine-2,4-dione;
9-(p-Methoxybenzyl)-1,3-di-n-propyl-7-iso-butyl-6-hydroxy-9H-8-oxopyrimido[2,1-f]purine-2,4-dione;
9-(p-Methoxybenzyl)-1,3-di-n-propyl-7-n-pentyl-6-hydroxy-9H-8-oxopyrimido[2,1-f]purine-2,4-dione;
9-(n-Butyl)-1,3-di-n-propyl-7-phenyl-6-hydroxy-9H-8-oxo-pyrimido[2,1-f]purine-2,4-dione;
9-(n-Butyl)-1,3-di-n-propyl-7-benzyl-6-hydroxy-9H-8-oxo-pyrimido[2,1-purine-2,4-dione;
9-Benzyl-1,3-di-n-butyl-7-ethyl-6-hydroxy-9H-8-oxo-pyrimido[2,1-f]purine-2,4-dione;
9-Benzyl-1,3-di-n-butyl-7-n-propyl-6-hydroxy-9H-8-oxo-pyrimido[2,1-f]purine-2,4-dione, m.p. 115° C.;
9-Benzyl-1,3-di-n-butyl-7-iso-propyl-6-hydroxy-9H-8-oxo-pyrimido[2,1-f]purine-2,4-dione;
9-Benzyl-6-hydroxy-1,3,7-tri-n-butyl-9H-8-oxo-pyrimido[2,1-f]purine-2,4-dione, m.p. 121° C.;
9-Benzyl-1,3-di-n-butyl-7-iso-butyl-6-hydroxy-9H-8-oxopyrimido[2,1-f]purine-2,4-dione;
9-Benzyl-1,3-di-n-butyl-7-sec-butyl-6-hydroxy-9H-8-oxopyrimido[2,1-f]purine-2,4-dione;
9-Benzyl-1,3-di-n-butyl-7-n-pentyl-6-hydroxy-9H-8-oxopyrimido[2,1-f]purine-2,4-dione;
9-Benzyl-1,3-di-n-butyl-7-iso-pentyl-6-hydroxy-9H-8-oxopyrimido[2,1-f]purine-2,4-dione;
9-Benzyl-1,3-di-n-butyl-7-n-hexyl-6-hydroxy-9H-8-oxopyrimido[2,1-f]purine-2,4-dione;
9-Benzyl-1,3-di-n-butyl-7-n-heptyl-6-hydroxy-9H-8-oxopyrimido[2,1-f]purine-2,4-dione;
9-Benzyl-1,3-di-n-butyl-7-n-octyl-6-hydroxy-9H-8-oxopyrimido[2,1-f]purine-2,4-dione;
9-(p-Fluorobenzyl)-1,3-di-n-butyl-7-methyl-6-hydroxy-9H-8-oxopyrimido[2,1-f]purine-2,4-dione; m.p. 175° C.;
9-(p-Fluorobenzyl)-1,3-di-n-butyl-7-n-propyl-6-hydroxy-9H-8-oxopyrimido[2,1-f]purine-2,4-dione; m.p. 130.5° C.;
9-(p-Fluorobenzyl)-1,3,7-tri-n-butyl-6-hydroxy-9H-8-oxopyrimido[2,1-f]purine-2,4-dione; m.p. 138° C.;
9-(p-Chlorobenzyl)-1,3-di-n-butyl-7-methyl-6-hydroxy-9H-8-oxopyrimido[2,1-f]purine-2,4-dione;
9-(p-Chlorobenzyl)-1,3-di-n-butyl-7-n-propyl-6-hydroxy-9H-8-oxopyrimido[2,1-f]purine-2,4-dione;
9-(p-Methoxybenzyl)-1,3-di-n-butyl-7-methyl-6-hydroxy-9H-8-oxopyrimido[2,1-f]purine-2,4-dione; m.p. 157° C.;
9-(p-Methoxybenzyl)-1,3-di-n-butyl-7-n-propyl-6-hydroxy-9H-8-oxopyrimido[2,1-f]purine-2,4-dione, m.p. 138° C.;
9-(n-Propyl)-1,3-di-n-butyl-7-phenyl-6-hydroxy-9H-8-oxopyrimido[2,1-f]purine-2,4-dione;
9-(n-Propyl)-1,3-di-n-butyl-7-benzyl-6-hydroxy-9H-8-oxopyrimido[2,1-f]purine-2,4-dione;
9-Benzyl-1-iso-butyl-3-methyl-7-ethyl-6-hydroxy-9H-8-oxopyrimido[2,1-f]purine-2,4-dione;
9-Benzyl-1-iso-butyl-3-methyl-7-n-propyl-6-hydroxy-9H-8-oxopyrimido[2,1-f]purine-2,4-dione;
9-Benzyl-1-iso-butyl-3-methyl-7-n-butyl-6-hydroxy-9H-8-oxopyrimido[2,1-f]purine-2,4-dione;
9-Benzyl-1-iso-butyl-3-methyl-7-n-pentyl-6-hydroxy-9H-8-oxopyrimido[2,1-f]purine-2,4-dione;
9-Benzyl-1-iso-butyl-3,7-dimethyl-6-hydroxy-9H-8-oxopyrimido[2,1-f]purine-2,4-dione;
9-Phenyl-1-iso-butyl-3,7-dimethyl-6-hydroxy-9H-8-oxopyrimido[2,1-f]purine-2,4-dione;
9-Phenyl-1-iso-butyl-3-methyl-7-n-propyl-6-hydroxy-9H-8-oxopyrimido[2,1-f]purine-2,4-dione;
9-Phenyl-1-iso-butyl-3-methyl-7-n-butyl-6-hydroxy-9H-8-oxopyrimido[2,1-f]purine-2,4-dione;
9-(n-Butyl)-1-iso-butyl-3-methyl-7-phenyl-6-hydroxy-9H-8-oxopyrimido[2,1-f]purine-2,4-dione;
9-(n-Butyl)-1-iso-butyl-3-methyl-7-benzyl-6-hydroxy-9H-8-oxopyrimido[2,1-f]purine-2,4-dione;
1-Phenyl-3-methyl-9-benzyl-7-n-propyl-6-hydroxy-9H-8-oxopyrimido[2,1-f]purine-2,4-dione;
3-Phenyl-1-methyl-9-benzyl-7-n-propyl-6-hydroxy-9H-8-oxopyrimido[2,1-f]purine-2,4-dione;
1-Benzyl-3-methyl-9-(p-fluorobenzyl)-7-n-propyl-6-hydroxy-9H-8oxopyrimido[2,1-f]purine-2,4-dione;
3-Benzyl-1-methyl-9-(p-fluorobenzyl)-7-n-propyl-6-hydroxy-9H-8-oxopyrimido[2,1-f]purine-2,4-dione;
1-(3-Pyridylmethyl)-3-methyl-9-benzyl-7-n-propyl-6-hydroxy-9H-8-oxopyrimido[2,1-f]purine-2,4-dione;
3-(3-Pyridylmethyl)-1-methyl-9-benzyl-7-n-propyl-6-hydroxy-9H-8-oxopyrimido[2,1-f]purine-2,4-dione;
1-(2-Thiophene-methyl)-3-methyl-9-benzyl-7-n-propyl-6-hydroxy-9H-8-oxopyrimido[2,1-f]purine-2,4-dione;
3-(2-Thiophene-methyl)-1-methyl-9-benzyl-7-n-propyl-6-hydroxy-9H-8-oxopyrimido[2,1-f]purine-2,4-dione;
1-(Cyclopropylmethyl)-3-methyl-9-benzyl-7-n-propyl-6-hydroxy-9H-8-oxopyrimido[2,1-f]purine-2,4-dione;
3-(Cyclopropylmethyl)-1-methyl-9-benzyl-7-n-propyl-6-hydroxy-9H-8-oxopyrimido[2,1-f]purine-2,4-dione;
1-Allyl-3-methyl-9-benzyl-7-n-propyl-6-hydroxy-9H-8-oxopyrimido[2,1-f]purine-2,4-dione;
3-Allyl-1-methyl-9-benzyl-7-n-propyl-6-hydroxy-9H-8-oxopyrimido[2,1-f]purine-2,4-dione;
1-Methyl-9-benzyl-7-n-propyl-6-hydroxy-9H-8-oxopyrimido[2,1-f]purine-2,4-dione;
3-Methyl-9-benzyl-7-n-propyl-6-hydroxy-9H-8-oxopyrimido[2,1-f]purine-2,4-dione;
9-Benzyl-7-n-propyl-6-hydroxy-9H-8-oxopyrimido[2,1-f]-purine-2,4-dione;
1,3-Diethyl-9-benzyl-6-hydroxy-9H-8-oxopyrimido[2,1-f]purine-2,4-dione;
1,3-Di-n-propyl-9-benzyl-6-hydroxy-9H-8-oxopyrimido[2,1-f]purine-2,4-dione;
1,3-Di-n-butyl-9-benzyl-6-hydroxy-9H-8-oxopyrimido[2,1-f]purine-2,4-dione;
1,3-Dimethyl-9-benzyl-7-[2-pyridylethyl]-6-hydroxy-9H-8-oxopyrimido[2,1-f]purine-2,4-dione;
1,3-Dimethyl-9-(p-fluorobenzyl)-7-[2-pyridylethyl]-6-hydroxy-9H-8-oxopyrimido[2,1-f]purine-2,4-dione;
1,3-Dimethyl-9-benzyl-7-[2-thiophene-methyl]-6-hydroxy-9H-8-oxopyrimido[2,1-f]purine-2,4-dione;
1,3-Dimethyl-9-cyclopentylmethyl-6-hydroxy-7-n-butyl-9H-8-oxopyrimido[2,1-f]purine-2,4-dione;
1,3-Dimethyl-9-cyclopropylmethyl-6-hydroxy-7-n-propyl-9H-8-oxopyrimido[2,1-f]purine-2,4-dione;
1,3-Dimethyl-9-cyclophenyl-6-hydroxy-7-n-propyl-9H-8-oxopyrimido[2,1-f]purine-2,4-dione;
1,3-Dimethyl-9-cyclohexyl-6-hydroxy-7-benzyl-9H-8-oxopyrimido[2,1-f]purine-2,4-dione;
1,4-Di-n-propyl-9-cyclooctyl-6-hydroxy-7-n-butyl-9H-8-oxopyrimido[2,1-f]purine-2,4-dione;
9-Benzyl-1,3-dimethyl-7-(3,3,3-trifluoropropyl)-6-hydroxy-9H-8-oxopyrimido[2,1-f]purine-2,4-dione;

9-(3-Pyridyl)-1,3-dimethyl-7-(n-propyl)-6-hydroxy-9H-8-oxopyrimido[2,1-f]purine-2,4-dione;

9-(p-Nitrobenzyl)-1,3-dimethyl-7-(n-propyl)-6-hydroxy-9H-8-oxopyrimido[2,1-f]purine-2,4-dione;

9-(p-Cyanobenzyl)-1,3-dimethyl-7-(n-propyl)-6-hydroxy-9H-8-oxopyrimido[2,1-f]purine-2,4-dione;

9-(2,5-Dimethylbenzyl)-1,3-dimethyl-7-(n-propyl)-6-hydroxy-9H-8-oxopyrimido[2,1-f]purine-2,4-dione;

9-(4-Biphenylmethyl)-1,3-dimethyl-7-(n-propyl)-6-hydroxy-9H-8-oxopyrimido[2,1-f]purine-2,4-dione;

9-(4-Allyloxybenzyl)-1,3-dimethyl-7-(n-propyl)-6-hydroxy-9H-8-oxopyrimido[2,1-f]purine-2,4-dione;

9-(4-Propargyloxybenzyl)-1,3-dimethyl-7-(n-propyl)-6-hydroxy-9H-8-oxopyrimido[2,1-f]purine-2,4-dione;

1,3-Dimethyl-9-(2-fluorobenzyl)-6-hydroxy-7-methyl-9H-8-oxopyrimido[2,1-f]purine-2,4-dione; m.p. 224° C.

1,3-Dimethyl-9-(3-fluorobenzyl)-6-hydroxy-7-n-propyl-9H-8-oxopyrimido[2,1-f]purine-2,4-dione; m.p. 213° C.

1,3-Dimethyl-9-(3-fluorobenzyl)-6-hydroxy-7-methyl-9H-8-oxopyrimido[2,1-f]purine-2,4-dione-½hydrate; m.p. 219° C.

1,3-Dimethyl-9-alpha-phenethyl-6-hydroxy-7-n-propyl-9H-8-oxopyrimido[2,1-f]purine-2,4-dione; m.p. 197° C.

7-(2-N,N-dimethylaminoethyl)-1,3-dimethyl-9-benzyl-6-hydroxy-9H-8-oxopyrimido[2,1-f]purine-2,4-dione; m.p. 195° C. (decomposes)

1,3-Dimethyl-9-(3,4-dichlorobenzyl)-6-hydroxy-7-n-butyl-9H-8-oxopyrimido[2,1-f]purine-2,4-dione; m.p. 214° C.

1,3-Dimethyl-9-(2,4-dichlorobenzyl)-6-hydroxy-7-n-butyl-9H-8-oxopyrimido[2,1-f]purine-2,4-dione; m.p. 220° C.

1,3-Dimethyl-9-cyclohexylmethyl-6-hydroxy-7-n-butyl-9H-8-oxopyrimido[2,1-f]purine-2,4-dione; m.p. 151° C.

1,3-Di-n-butyl-7-n-butyl-6-hydroxy-9-(4-methoxybenzyl)-9H-8-oxopyrimido[2,1-f]purine-2,4-dione; m.p. 129° C.

1,3-Dimethyl-6-hydroxy-9-n-butyl-7-n-propyl-9H-8-oxopyrimido[2,1-f]purine-2,4-dione-sodium salt; m.p. 245°–260° C.

1,3-Di-n-butyl-6-hydroxy-7-methyl-9-thiophenylmethyl-9H-8-oxopyrimido[2,1-f]purine-2,4-dione; m.p. 102° C.

1,3-Di-n-butyl-6-hydroxy-7-n-propyl-9-thiophenylmethyl-9H-8-oxopyrimido[2,1-f]purine-2,4-dione; m.p. 115° C.

1,3-Di-n-butyl-6-hydroxy-7-isopentyl-9-thiophenylmethyl-9H-8-oxopyrimido[2,1-f]purine-2,4-dione; m.p. 135° C.

1,3-Dimethyl-6-hydroxy-7-methyl-9-(2-phenyl)-9H-8-oxopyrimido[2,1-f]purine-2,4-dione; m.p. 222° C.

1,3-Dimethyl-6-hydroxy-7-isobutyl-9-(2-phenethyl)-9H-8-oxopyrimido[2,1-f]purine-2,4-dione; m.p. 197° C.

1,3-Di-n-butyl-6-hydroxy-7-n-propyl-9-(2-phenethyl)-9H-8-oxopyrimido[2,1-f]purine-2,4-dione; m.p. 117° C.

1,3-Di-n-butyl-6-hydroxy-7-n-butyl-9-(2-phenethyl)-9H-8-oxopyrimido[2,1-f]purine-2,4-dione; m.p. 81° C.

1,3-Dimethyl-6-hydroxy-7-n-propyl-9-(2-phenethyl)-9H-8-oxopyrimido[2,1-f]purine-2,4-dione; m.p. 168° C.

1,3-Dimethyl-6-hydroxy-7-isopropyl-9-(2-phenethyl)-9H-8-oxopyrimido[2,1-f]purine-2,4-dione; m.p. 209° C.

1,3-Di-n-butyl-6-hydroxy-7-methyl-9-(2-phenethyl)-9H-8-oxopyrimido[2,1-f]purine-2,4-dione; m.p. 126° C.

9-(4-[2-Phenethyloxy]-benzyl)-1,3-dimethyl-7-(n-propyl)-6-hydroxy-9H-8-oxopyrimido[2,1-f]purine-2,4-dione;

9-(2-Naphthylmethyl)-1,3-dimethyl-7-(n-propyl)-6-hydroxy-9H-8-oxopyrimido[2,1-f]purine-2,4-dione;

9-(9-Phenanthrenylmethyl)-1,3-dimethyl-7-(n-propyl)-6-hydroxy-9H-8-oxopyrimido[2,1-f]purine-2,4-dione;

9-(3-Quinolinyl)-1,3-dimethyl-7-(n-propyl)-6-hydroxy-9H-8-oxopyrimido[2,1-f]purine-2,4-dione;

9-(5-Isoquinolinyl)-1,3-dimethyl-7-(n-propyl)-6-hydroxy-9H-8-oxopyrimido[2,1-f]purine-2,4-dione;

9-[2-(5-Methyl-1,3,4-thiodiazolyl)]-1,3-dimethyl-7-(n-propyl)-6-hydroxy-9H-8-oxopyrimido[2,1-f]purine-2,4-dione;

9-(2-Thiazolyl)-1,3-dimethyl-7-(n-propyl)-6-hydroxy-9H-8-oxopyrimido[2,1-f]purine-2,4-dione; and 9-(3-Thiaphenemethyl)-1,3-dimethyl-7-(n-propyl)-6-hydroxy-9H-8-oxopyrimido[2,1-f]purine-2,4-dione.

9-(2-fluorobenzyl)-1,3,7-trimethyl-6-hydroxy-8-oxopyrimido[2,1-f]purine-2,4-dione, m.p. 224°–226° C.;

9-(3-fluorobenzyl)-1,3,dimethyl-7-n-propyl-6-hydroxy-8-oxopyrimido[2,1-f]purine-2,4-dione, m.p. 213°–214.5° C.;

9-(3-fluorobenzyl)-1,3,7-trimethyl-6-hydroxy-8-oxopyrimido[2,1-f]purine-2,4-dione-¼ hydrate, m.p. 218°–219.5° C.;

9-(1-phenethyl)-1,3,-dimethyl-7-n-propyl-6-hydroxy-8-oxopyrimido[2,1-f]purine-2,4-dione, m.p. 197°–200° C.;

9-Benzyl-1,3-dimethyl-7-(N,N-dimethyl-2-ethylamino)-6-hydroxy-8-oxopyrimido[2,1-f]purine-2,4-dione-hydrochloride, m.p. 195°–197° C. (decomposes);

9-(3,4-Dichlorobenzyl)-1,3-dimethyl-7-n-butyl-6-hydroxy-8-oxopyrimido[2,1-f]purine-2,4-dione, m.p. 214°–216° C.;

9-(2,4-Dichlorobenzyl)-1,3-dimethyl-7-n-butyl-6-hydroxy-8-oxopyrimido[2,1-f]purine-2,4-dione, m.p. 220°–222° C.;

9-(4-chlorobenzyl)-1,3,7-trimethyl-6-hydroxy-8-oxopyrimido[2,1-f]purine-2,4-dione, m.p. 236°–238° C.;

9-(4-methoxybenzyl)-1,3,7-tri-n-butyl-6-hydroxy-8-oxopyrimido[2,1-f]purine-2,4-dione, m.p. 129°–131° C.;

9-(Thiophenylmethyl)-1,3-di-n-butyl-7-methyl-6-hydroxy-8-oxopyrimido[2,1-f]purine-2,4-dione, m.p. 100.5°–102° C.;

9-(Thiophenylmethyl)-1,3-di-n-butyl-7-n-propyl-6-hydroxy-8-oxopyrimido[2,1-f]purine-2,4-dione, m.p. 115°–117° C.;

9-(Thiophenylmethyl)-1,3-di-n-butyl-7-iso-pentyl-6-hydroxy-8-oxopyrimido[2,1-f]purine-2,4-dione, m.p. 133.5°–135° C.;

9-(2-phenethyl)-1,3,7-trimethyl-6-hydroxy-8-oxopyrimido[2,1-f]purine-2,4-dione m.p. 222°–224° C.;

9-(2-phenethyl)-1,3-dimethyl-7-isopentyl-6-hydroxy-8-oxopyrimido[2,1-f]purine-2,4-dione m.p. 197°–198.5° C.;

9-(2-phenethyl)-1,3-di-n-butyl-7-n-propyl-6-hydroxy-8-oxopyrimido[2,1-f]purine-2,4-dione, m.p. 117°–118.5° C.;

9-(2-phenethyl)-1,3,7-tri-n-butyl-6-hydroxy-8-oxopyrimido[2,1-f]purine-2,4-dione, m.p. 81°–83° C.;

9-(2-phenethyl)-1,3-dimethyl-7-n-propyl-6-hydroxy-8-oxopyrimido[2,1-f]purine-2,4-dione, m.p. 168°–170° C.;

9-(2-phenethyl)-1,3-dimethyl-7-iso-propyl-6-hydroxy-8-oxopyrimido[2,1-f]purine-2,4-dione m.p. 209°–211° C.;

9-(2-phenethyl)-1,3-di-n-butyl-7-methyl-6-hydroxy-8-oxopyrimido[2,1-f]purine-2,4-dione m.p. 126°–128° C.

EXAMPLE 3

9-Benzyl-1,3-dimethyl-7-(2-ethoxyethyl)6-hydroxy-9H-8-oxo-pyrimido[2,1-f]purine-2,4-dione To a stirred suspension of 7.43 gm of 8-benzylaminotheophylline in 104 ml of dry N,N-dimethylformamide there is added portionwise over 10 minutes 1.19 gm of a 60% dispersion of sodium hydride. Heat the mixture to 50° C. under a nitrogen atmosphere for 30 minutes. Add 13.30 gm of the diethyl ester of β-ethoxyethylmalonic acid. Heat the mixture to 150° C. under a nitrogen atmosphere for approximately 37 hours. Allow the system to cool to room temperature and remove the solvent in vacuo. Add a mixture of water-chloroform (1:2.5) to the resulting semisolid. The aqueous portion is acidified with 3M HCl. Extract the product from the aqueous portion with chloroform. Wash the chloroform extracts with brine, dry over anhydrous sodium sulfate, filter and remove the solvent in vacuo to give the crude product. Triturate the crude product with ether. Purify the crude product by column chromatography on silica gel and triturate the major fraction with hexane to give the title compound, m.p. 156.5°–157.5° C.

Similarly, prepare the following:

9-Benzyl-1,3-dimethyl-7-ethoxycarbonyl-6-hydroxy-8-oxo-pyrimido[2,1-f]purine-2,4-dione sodium salt·hydrate, m.p. >240° C. (decomposes)

9-Benzyl-1,3-dimethyl-7-(2-ethylthioethyl)-6-hydroxy-9H-8-oxo-pyrimido[2,1-f]purine-2,4-dione·¼ hydrate sodium salt, m.p. 298° C. (decomposes)

9-Benzyl-1,3-dimethyl-7-(2-ethoxyethyl)6-hydroxy-9H-8-oxo-pyrimido[2,1-f]purine-2,4-dione, m.p. 156.5°–157.5° C.;

Also, similarly prepare the following:

1,3-Dimethyl-9-benzyl-7-(2-ethylthioethyl)-6-hydroxy-9H-8-oxopyrimido[2,1-f]purine-2,4-dione;

1,3-Dimethyl-9-benzyl-7-(n-propylthioethyl)-6-hydroxy-9H-8-oxopyrimido[2,1-f]purine-2,4-dione;

1,3-Dimethyl-9-benzyl-7-(n-butylthiomethyl)-6-hydroxy-9H-8-oxopyrimido[2,1-f]purine-2,4-dione;

1,3-Dimethyl-9-benzyl-7-(n-butoxymethyl)-6-hydroxy-9H-8-oxopyrimido[2,1-f]purine-2,4-dione;

1,3-Dimethyl-9-benzyl-7-(4-hydroxy-n-butyl)-6-hydroxy-9H-8-oxopyrimido[2,1-f]purine-2,4-dione;

1,3-Dimethyl-9-benzyl-7-(2-hydroxyethyl)-6-hydroxy-9H-8-oxopyrimido[2,1-f]purine-2,4-dione; m.p. 184° C. (decomposes)

9-Benzyl-1,3-diethyl-7-(2-hydroxyethyl)-6-hydroxy-9H-8-oxypyrimido[2,1-f]purine-2,4-dione;

9-Benzyl-2,3-dimethyl-7-(3-hydroxypropyl)-6-hydroxy--9H-8-oxypyrimido[2,1-f]purine--2,4-dione;

9-(p-Chlorobenzyl)-1,3-dimethyl-7-(2-hydroxypropyl)-6-hydroxy-9H-8-oxopyrimido[2,1-f]purine-2,4-dione;

9-(p-Fluorobenzyl)-1,3-dimethyl-7-(2-hydroxyethyl)-6-hydroxy-9H-8-oxopyrimido[2,1-f]purine-2,4-dione;

EXAMPLE 4

7-(2-Acetoxyethyl)-9-benzyl-1,3-dimethyl-6-hydroxy-9H-8-oxo-pyrimido[2,1-f]purine-2,4-dione Suspend 9-benzyl-1,3-dimethyl-7-(2-hydroxyethyl)-6-hydroxy-9H-8-oxo-pyrimido[2,1-f]purine-2,4-dione (2 g.) in tetrahydrofuran (35 ml.) at 0°–5° C. Add acetyl chloride (0.593 g.) and then triethylamine (1.05 ml.) to the reaction mixture at 0°–5° C. Stir at 0°–5° C. for approximately 10 minutes and then allow the reaction mixture to warm to room temperature, stirred at room temperature overnight. Dilute the reaction mixture with ether (10 ml) and filter. Remove the filtrate in vacuo. Dissolve the solid with ethyl acetate and wash the organic solution with brine. Remove the ethyl acetate in vacuo. Chromatograph the crude product on silica gel using 96.95:3:0.05 chloroform methanol:acetic acid to give the title compound, m.p. 68° C.

Similarly, prepare the following by using the appropriate 7-hydroxyalkyl compounds:

7-(3-Acetoxypropyl)-9-benzyl-1,3-dimethyl-6-hydroxy-H-8-oxopyrimido[2,1-f]purine-2,4-dione;

7-(2-Acetoxypropyl)-9-(p-chlorobenzyl)-1,3-dimethyl-6-hydroxy-9H-8-oxopyrimido[2,1-f]purine-2,4-dione; and 7-(2-Acetoxyethyl)-1,3-dimethyl-9-(p-fluorobenzyl)-6-hydroxy-9H-8-oxopyrimido[2,1-f]purine-2,4-dione.

By substituting other acid anhydrides or chlorides in the above procedure, other 7-acyloxyalkyl derivatives may be prepared.

This same process may be used to acylate phenolic derivatives to produce the $C_1$ to $C_6$ alkoxy substituted aryl derivatives. Such products include:

9-(4-Acetoxybenzyl)-1,3-dimethyl-7-(n-propyl)-6-hydroxy-9H-8-oxopyrimido[2,1-f]purine-2,4-dione; and 9-(4-Propionyloxybenzyl)-1,3-dimethyl-7-(n-propyl)-6-hydroxy-9H-8-oxopyrimido[2,1-f]purine-2,4-dione.

This process may also be used to prepare the "($C_1$ to $C_6$ acyloxy)-($C_1$ to $C_6$ alkyl)" derivatives from the "hydroxy($C_1$ to $C_6$ alkyl)" derivatives. Examples of such products are:

9-(4-Acetoxymethylbenzyl)-1,3-dimethyl-7-(n-propyl)-6-hydroxy-9H-8-oxopyrimido[2,1-f]purine-2,4-dione; and 9-(4-Acetoxymethylphenyl)-1,3-dimethyl-7-(n-propyl)-6-hydroxy-9H-8-oxopyrimido[2,1-f]purine-2,4-dione.

EXAMPLE 5

9-(4-Fluorobenzyl)-1,3,7-trimethyl-6-acetoxy-9H-8-oxopyrimido[2,1-f]purine-2,4-dione Dissolve 9-(4-fluorobenzyl)-1,3,7-trimethyl-9H-8-oxopyrimido[2,1-f]purine-2,4-dione (1 g.) in pyridine (20 ml) containing acetic anhydride (8 ml.). Heat the solution to reflux overnight, then pour into 10% HCl solution. Wash the solids, dry, and chromatograph on silica gel in methylene chloride (95%):acetone (5%) to yield the title compound, m.p. 228°–230.5° C., as the hemihydrate.

In a similar manner, prepare any of the compounds of this invention wherein $R_5$ is acyl or aroyl, for example 9-Benzyl-1,3-dimethyl-7-n-propyl-6-acetoxy-9H-8-oxopyrimido[2,1-f]purine-2,4-dione.

EXAMPLE 6

1,3-Dimethyl-6-methoxy-9-benzyl-7-n-propyl-9H-8-oxopyrimido[2,1-f]purine-2,4-dione 1,3-Dimethyl-6-hydroxy-9-benzyl-7-n-propyl-9H-8-oxopyrimido[2,1-f]purine-2,4-dione (3 g) dissolved in 200 ml chloroform at 0° is treated with an etheral solution of diazomethane. The solution is stirred at 0° for 1.5 hours and the excess diazomethane is destroyed by the addition of acetic acid. The chloroform solution is washed with a solution of sodium bicarbonate and the chloroform is removed under reduced pressure. The solid obtained is chromatographed on silica gel using 1% methanol in chloroform to give the title compound, m.p. 199°–201° C.

Similarly, prepare the following:
1,3-Dimethyl-6-methoxy-9-(4-fluorobenzyl)-7-n-propyl-9H-8-oxopyrimdo[2,1-f]purine-2,4-dione;
1,3-Di-n-butyl-6-methoxy-9-benzyl-7-n-butyl-9H-8-oxopyrimido[2,1-f]purine-2,4-dione;
1,3-Di-n-butyl-6-methoxy-9-(4-fluorobenzyl)-7-n-butyl-9H-8-oxopyrimido[2,1-f]purine-2,4-dione;
1,3-Dimethyl-6-ethoxy-9-(4-fluorobenzyl)-7-n-propyl-9H-8-oxopyrimido[2,1-f]purine-2,4-dione;
1,3-Di-n-propyl-6-ethoxy-9-thiophenlmethyl-7-n-propyl-9H-8-oxopyrimido[2,1-f]purine-2,4-dione;
9-Benzyl-1,3-dimethyl-7-n-propyl-6-n-butoxy-9H-8-oxo-pyrimido[2,1-f]purine-2,4-dione.

EXAMPLE 7

9-Benzyl-1,3-dimethyl-6-hydroxy-7-prenyl-9H-8-oxopyrimido[2,1-f]purine-2,4-dione Suspend 9-benzyl-1,3-dimethyl-6-hydroxy-9H-8-oxopyrimido[2,1-f]purine-2,4-dione (10 g.) in 150 ml of N,N-dimethylformamide. Add sodium hydride (1.6 gm-50% suspension) to the reaction mixture and stir the system at room temperature for 15–30 minutes under a nitrogen atmosphere. Add prenyl bromide (5 ml). Stir the reaction mixture at room temperature under a nitrogen atmosphere for 20 hours. Pour the reaction mixture into ice-water. Collect the precipitate and dissolve it in chloroform. Wash the chloroform solution with water, dry the solution over magnesium sulfate, filter and remove the solvent in vacuo. Chromatograph the crude product on silica gel using chloroform/methanol 95:5. The product is recrystallized from chloroform/ethyl acetate to give the title compound, m.p. 186°–188° C.

Similarly, prepare the following:
9-Benzyl-1,3-dimethyl-6-hydroxy-7-allyl-9H-8-oxopyrimido[2,1-f]purine-2,4-dione, m.p. 222°–224° C.;
9-Benzyl-1,3-dimethyl-6-hydroxy-7-propargyl-9H-8-oxo pyrimdo [2,1-f]purine-2,4-dione, m.p. 236°–238° C.; (stoichiometric amount of 18-crown-6 is added to reaction mixture)
9-Benzyl-1,3-dimethyl-6-hydroxy-7-(2-butenyl)-9H-8-oxopyrimido[2,1-f]purine-2,4-dione, m.p. 206°–208° C.;
1,3-Dimethyl-9-(4-fluorobenzyl)-6-hydroxy-7-prenyl-9H-8-oxopyrimido[2,1-f]purine-2,4-dione, m.p. 232°–234° C.;
9-Benzyl-1,3-dimethyl-6-hydroxy-7-(cyclohex-2-enyl)-9H-8-oxopyrimido[2,1-f]purine-2,4-dione, m.p. 157°–161° C.;
1,3-Dimethyl-7,9-dibenzyl-6-hydroxy-9H-8-oxopyrimido[2,1-f]purine-2,4-dione, m.p. 190°–195° C.; (stoichiometric amount of 18-crown-6 is added to reaction mixture).

EXAMPLE 8

9-Benzyl-1,3-dimethyl-6-hydroxy-7-cyanomethyl-9H-8-oxopyrimido[2,1-f]purine-2,4-dione Suspend 9-benzyl-1,3-dimethyl-6-hydroxy-9H-8-oxopyrimido[2,1-f]purine-2,4-dione (6.14 g.) in 125 ml. of N,N-dimethylformamide. Add sodium hydride (0.696 g. 60% NaH) to the reaction mixture and stir the system at room temperature for 15–30 minutes under a nitrogen atmosphere. Add bromocyanomethane (2.3 g.). Stir the reaction mixture at 80° C. under a nitrogen atmosphere for 18 hours. Remove the solvent in vacuo. Triturate the residue with ether. Filter the solids and then dissolve the solids in chloroform-methanol-ammonia (85:20:1). Chromatograph the product using chloroform:methanol:ammonia (85:20:1). Recrystallize the product from methanol/acetonitrile to give the title compound, m.p. 195° C. (decomposes).

Similarly, prepare the following:
9-Benzyl-1,3-dimethyl-6-hydroxy-7-methoxycarbonyl methyl-9H-8-oxopyrimido[2,1-f]purine-2,4-dione; m.p. 211°–214.5° C.

EXAMPLE 9

9-Benzyl-1,3-dimethyl-6-hydroxy-7-prenyl-9H-8-oxopyrimido[2,1-f]purine-2,4-dione sodium salt Dissolve 9-benzyl-1,3-dimethyl-6-hydroxy-7-prenyl-9H-8-oxopyrimido[2,1-f]purine-2,4-dione (3.4 g.) in an aqueous solution (450 ml.). Add 1N sodium hydroxide (7.8 ml.). Stir the solution at room temperature for 75 hours. Filter the solution and lyophilize the filtrate to give the title compound, m.p. 240°–260° C.

Similarly, prepare the following:
9-Benzyl-1,3-dimethyl-6-hydroxy-7-allyl-9H-8-oxoypyrimido[2,1-f]purine-2,4-dione sodium salt, m.p. 280°–300° C.;
9-Benzyl-1,3-dimethyl-6-hydroxy-7-(2-butenyl)-9H-8-oxopyrimido[2,1-f]purine-2,4-dione sodium salt, m.p. 260°–280° C.;
9-Benzyl-1,3-dimethyl-6-hydroxy-7-(cyclohex-2-enyl)-9H-8-oxopyrimido[2,1-f]purine-2-4-dione sodium salt, m.p. 280°–300° C.;
9-n-pentyl-1,3-dimethyl-7-n-propyl-6-hydroxy-8-oxopyrimido[2,1-f]purine-2,4-dione sodium salt, m.p. 245°–260° C.;
9-Benzyl-1,3-dimethyl-6-hydroxy-8-oxopyrimido[2,1-f]purine-2,4-dione sodium salt·hydrate, m.p. >295° C.;
9-(4-Fluorobenzyl)-1,3-dimethyl-6-hydroxy-8-pyrimido[2,1-f]-2,4-dione sodium salt·hydrate, m.p. 260°–280° C.;
9-Benzyl-1,3-dimethyl-6-hydroxy-7-methoxycarbonyl-methyl-9H-8-oxopyrimido[2,1-f]purine-2,4-dione sodium salt, m.p. 227°–230° C. (decomposes);
1,3-dimethyl-9-(4-fluorobenzyl)-6-hydroxy-7-prenyl-9H-8-oxopyrimido[2,1-f]purine-2,4-dione sodium salt, m.p. 260°–280° C.

Similarly, prepare the following:
9-Benzyl-1,3-dimethyl-6-hydroxy-7-propargyl-9H-8-oxopyrimido[2,1-f]purine-2,4-dione potassium salt;
9-Benzyl-1,3-dimethyl-6-hydroxy-7-prenyl-9H-8-oxopyrimido[2,1-f]purine-2,4-dione potassium salt;
9-Benzyl-1,3-dimethyl-6-hydroxy-7-prenyl-9H-8-oxopyrimido[2,1-f]purine-2,4-dione sodium salt;

1,3-dimethyl-7,9-dibenzyl-6-hydroxy-9H-8-oxo-pyrimido[2,1-f]purine-2,4-dione sodium salt;
9-Benzyl-1,3-dimethyl-6-hydroxy-7-cyanomethyl-9H-8-oxopyrimido[2,1-f]purine-2,4-dione sodium salt.

EXAMPLE 10

9-Benzyl-1,3-dimethyl-6-hydroxy-9H-8-oxopyrimido[2,1-f]purine-2,4-dione-7-acetic acid Heat under a nitrogen atmosphere a solution of 3.33 g of 9-benzyl-7-carbomethoxymethyl-1,3-dimethyl-6-hydroxy-8-oxopyrimido-[2,1-f]purine-2,4-dione and 0.93 g of sodium hydroxide in 120 ml. of water at 60° C. for 2 hours, then allow mixture to stir at room temperature another 16 hours.

Dilute the reaction mixture with 20 ml of water and acidify to pH 2 with 7.5 ml of 3M HCl. Filter the resultant precipitate and wash the filter cake with 1:4 acetone-ether to obtain the title compound with m.p. 258° C. (d).

EXAMPLE 11

9-Benzyl-1,3-dimethyl-6-hydroxy-9H-8-oxopyrimido[2,1-f]purine-2,4-dione

Add 8-benzylaminotheophylline (30 gm.) and ethyl malonyl chloride (35.1 gm) to 600 ml of 1:1 dioxane/acetonitrile. Heat the reaction mixture to reflux under a nitrogen atmosphere until the 8-benzylaminotheophylline is consumed (Ca. 3.5 hrs.). Cool the reaction mixture to room temperature and pour the solution into 800 ml. of ether. Filter the precipitate. Wash the precipitate with ether and dry the product to obtain the title compound, m.p. 205.5°–209° C.

Similarly, prepare the following:
1,3-Dimethyl-6-hydroxy-9-(4-fluorobenzyl)-9H-9-oxopyrimido[2,1-f]purine-2,4-dione.

The anti-inflammatory potential of the compounds of the present invention may be determined by the Reversed Passive Arthus Reaction (RPAR) Synovitis technique as set forth below using male Lewis rats (obtained from Charles River Breeding Laboratories) weighing 200–250 grams. The potency of the compounds is determined using indomethacin as the standard. On the basis of the test results, a dosage range of about 0.1 milligrams per kilogram of body weight per day to about 50 milligrams per kilogram of body weight per day in divided doses taken at about 4 hour intervals is recommended.

Of course, the dosage to be administered depends upon the particular compound used, the age and general health of the patient and the severity of the inflammatory condition. Thus, the dose ultimately decided upon must be left to the judgment of a trained health-care practitioner.

RPAR SYNOVITIS TECHNIQUE

A Lewis rat is dosed orally with drug or placebo one hour prior to intravenous administration of 2.28 mg of bovine serum albumin (BSA) in 0.2 cc of pyrogen free saline followed by the intraarticular injection of 0.54 mg of rabbit anti-BSA antibody in 0.03 cc of pyrogen free saline into one knee joint. The contralateral knee is injected with 0.03 cc of pyrogen free saline. All injections are made with the animal under light ether anesthesia. Three hours later the rat is again dosed orally with drug or placebo. All drug doses are split. That is, one-half of the dose is administered before lesion induction and one-half is administered after lesion induction.

The following morning (about 17 hours after lesion induction) the rat is killed and both knee joints are exposed. The subpatellar areolar tissue with attendant synovium is excised and weighed. Differences between the weight of antibody and saline injected knees are considered to represent the inflammatory response for each animal (delta synovial weight). Differences in delta synovial weight between lesion controls and drug-treated rats are evaluated for statistical significance with an analysis of variance. Relative potencies are determined with a linear regression analysis.

The compounds of this invention may be processed and dispensed in tablets, capsules or elixirs, for oral administration; and solutions or suspensions for parenteral administration. In whatever form the compounds are dispensed, they may be admixed with the pharmaceutically acceptable excipients, binders, dispersing agents and carriers generally used in the art.

Exemplary of the pharmaceutical carriers, excipients, preservatives and binders are gelatin, lactose, starch, magnesium stearate, talc, vegetable oils, gums, polyalkylene glycols, etc. The pharmaceutical dosage forms are prepared by the methods conventionally used in the art. Further, the dosage units may also contain a compatible anti-depressant and/or analgesics to treat the depression and pain usually associated with chronic inflammatory conditions.

The following examples illustrate the preparation of solid dosage forms:

| No. | Ingredient | mg/capsule | mg/capsule |
|---|---|---|---|
| A. Capsules: | | | |
| 1. | Compound of the invention | 50 | 250 |
| 2. | Lactose USP | 50 | 100 |
| 3. | Corn Starch, Food Grade | 48.5 | 50 |
| 4. | Microcrystalline Cellulose NF | 50 | 95 |
| 5. | Magnesium Stearate NF | 1.5 | 5 |
| | Total | 200 | 500 |

Method of Manufacture

Mix Item Nos. 1, 2, 3 and 4 in a suitable mixer for 10–15 minutes. Add Item No. 5 and mix for 1–3 minutes. Fill the mixture into suitable two-piece hard gelatin capsules using encapsulating machine.

| No. | Ingredient | mg/capsule | mg/capsule |
|---|---|---|---|
| B. Tablets: | | | |
| 1. | Compound of the invention | 50 | 250 |
| 2. | Lactose USP | 68 | 57 |
| 3. | Corn Starch, Food Grade, as a 10% paste in Purified Water | 10 | 20 |
| 4. | Corn Starch, Food Grade | 20 | 18 |
| 5. | Magnesium Stearate NF | 2 | 5 |
| | Total | 150 | 350 |

Method of Manufacture

Mix Item Nos. 1 and 2 in a suitable mixer for 10–15 minutes. Granulate the mixture with Item No. 3. Pass the wet granulation through a coarse screen (e.g., ¼") if needed, and dry the wet granules. Mill the dried granules. Combine Item No. 4 and the dried granules and mix for 10–15 minutes. Add Item No. 5 and mix for 1–3 minutes. Compress the mixture to appropriate size and weight on a suitable tablet machine.

I claim:

1. A compound having the structural formula I

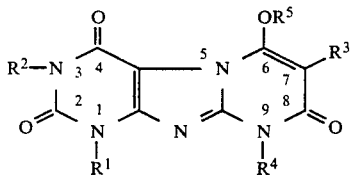

wherein

R[1] and R[2] are independently selected from hydrogen, cycloalkyl having from 3 to 8 carbon atoms, alkenyl having from 3 to 8 carbon atoms, alkynyl having from 3 to 8 carbon atoms, phenyl, substituted phenyl, alkyl having from 1 to 6 carbon atoms [which may be substituted with cycloalkyl having from 3 to 8 carbon atoms, phenyl, quinolinyl, isoquinolinyl, pyridyl, thiazolyl, 1,3,4-thiadiazolyl, thienyl and substituted phenyl, quinolinyl, isoquinolinyl, pyridyl, thiazolyl, 1,3,4-thiadiazolyl, and thienyl];

R[3] is hydrogen, formyl, cycloalkyl having from 3 to 8 carbon atoms, alkenyl having from 2 to 8 carbon atoms, alkynyl having from 3 to 8 carbon atoms, cycloalkenyl having from 5 to 8 carbon atoms, acyloxyalkyl having from 2 to 12 carbon atoms, —alkyl—X—$C_pH_{2p+1}$ (wherein the alkyl portion has 1 to 6 carbon atoms, p is an integer from 0 to 4, and X represents CO, O, S, $S^+$—$O^-$, $SO_2$ or —$NC_rH_{2r+1}$ wherein r is an integer from 0 to 4), —$(CH_2)_n$CONR[6]R[7] (wherein R[6] and R[7] are independently hydrogen or alkyl having from 1 to 6 carbon atoms, and n is an integer from 0 to 6), —$(CH_2)_m$C(O)OR[8] (wherein R[8] is hydrogen, alkyl having from 1 to 6 carbon atoms or a pharmaceutically acceptable metal or amine cation and m is an integer from 0 to 6), phenyl, substituted phenyl, alkyl having from 1 to 6 carbon atoms [which may be substituted with hydroxy, sulfhydryl, cyano, amino, halo, cycloalkyl having from 3 to 8 carbon atoms, phenyl, quinolinyl, isoquinolinyl, pyridyl, thiazolyl, 1,3,4-thiadiazolyl, thienyl and substituted phenyl, quinolinyl, isoquinolinyl, pyridyl, thiazolyl, 1,3,4-thiadiazolyl and thienyl];

R[4] is hydrogen, phenyl, quinolinyl, isoquinolinyl, pyridyl, thiazolyl, 1,3,4-thiadiazolyl, thienyl, and substituted phenyl, quinolinyl, isoquinolinyl, pyridyl, thiazolyl, 1,3,4-thiadiazolyl and thienyl, alkyl having from 1 to 6 carbon atoms [which may be substituted with cycloalkyl having from 3 to 8 carbon atoms, phenyl, quinolinyl, isoquinolinyl, pyridyl, thiazolyl, 1,3,4-thiadiazolyl, thienyl and substituted phenyl, quinolinyl, isoquinolinyl, pyridyl, thiazolyl, 1,3,4-thiadiazolyl and thienyl];

R[5] is hydrogen, alkyl having from 1 to 4 carbon atoms,

(wherein R[9] is alkyl having from 1 to 6 carbon atoms), or a pharmaceutically acceptable metal or amine cation.

2. A compound defined in claim 1 having the structural formula I and the pharmaceutically acceptable salts thereof, wherein R[1] and R[2] are independently selected from alkyl of 1 to 4 carbon atoms;

R[3] is alkenyl having from 2 to 8 carbon atoms, alkynyl having from 3 to 8 carbon atoms, cycloalkenyl having from 5 to 8 carbon atoms, —alkyl—X—$C_pH_{2p+1}$ (wherein the alkyl portion has 1 to 6 carbon atoms, p is an integer from 0 to 4, and X represents O, S, $S^+O^-$, $SO_2$ or —$NC_rH_{2r+1}$ (wherein r is an integer from 0 to 4)), —$(CH_2)_n$C(O)—NR[6]R[7] (wherein R[6] and R[7] are independently hydrogen or alkyl having from 1 to 6 carbon atoms, and n is an integer from 0 to 6), —$(CH_2)_m$C(O)OR[8] (wherein R[8] is alkyl having from 1 to 6 carbon atoms and m is an integer from 0 to 6), alkyl having from 1 to 6 carbon atoms which may be substituted with hydroxy or sulfhydryl; R[4] is alkyl having from 1 to 6 carbon atoms which is substituted with either phenyl or substituted phenyl; R[5] is hydrogen or a pharmaceutically acceptable cation.

3. A compound defined in claim 1 wherein R[1] and R[2] are alkyl of 1 to 3 carbon atoms.

4. A compound defined in claim 1 wherein R[1] and R[2] are methyl.

5. A compound defined in claim 1 wherein R[3] is alkenyl having from 3 to 8 carbon atoms, alkynyl having from 3 to 8 carbon atoms or alkyl having from 1 to 6 carbon atoms.

6. A compound defined in claim 1 wherein R[3] is n-propyl, n-butyl, propargyl (—$CH_2C\equiv CH$), allyl or prenyl (—$CH_2CH=C(CH_3)_2$).

7. A compound defined in claim 1 wherein R[4] is —$CH_2$—phenyl and —$CH_2$—substituted phenyl.

8. A compound defined in claim 1 wherein R[4] is benzyl or p-fluorobenzyl.

9. A compound defined in claim 3 wherein R[3] is alkenyl having from 3 to 8 carbon atoms, alkynyl having from 3 to 8 carbon atoms, or alkyl having from 1 to 6 carbon atoms.

10. A compound defined in claim 9 wherein R[3] is n-propyl, n-butyl, propargyl, allyl or prenyl.

11. A compound defined in claim 9 wherein R[4] is —$CH_2$—phenyl or —$CH_2$—substituted phenyl.

12. A compound defined in claim 9 wherein $R_4$ is benzyl or p-fluorobenzyl.

13. A compound defined in claim 10 wherein R[4] is —$CH_2$—phenyl or —$CH_2$—substituted phenyl.

14. A compound defined in claim 10 wherein R[4] is benzyl or p-fluorobenzyl.

15. A compound defined in claim 1 having the name:
9-(4-Fluorobenzyl)-1,3-dimethyl-6-hydroxy-7-(2-propynyl)-pyrimido-[2,1-f]purine-2,4,8-(1H,3H,9H)-trione;
9-Benzyl-1,3-dimethyl-6-hydroxy-7-(3-methyl-2-butenyl)pyrimido-[2,1-f]purine-2,4,8(1H,3H,9H)-trione;
9-Benzyl-1,3-dimethyl-6-hydroxy-7-(2-propynyl)-pyrimido[2,1-f]purine-2,4,8(1H,3H,9H)-trione;
9-(4-Fluorobenzyl)-6-hydroxy-1,3-dimethyl-7-(n-propyl)-9H-8-oxo-pyrimido[2,1-f]purine-2,4-dione;
9-(4-Fluorobenzyl)-1,3-dimethyl-6-hydroxy-7-(n-butyl)-9H-8-oxopyrimido[2,1-f]purine-3,4-dione;
9-Benzyl-1,3-dimethyl-8-hydroxy-7-(n-butyl)-9H-6-oxo-pyrimido[2,1-f]purine-2,4-dione;
9-Benzyl-1,3-dimethyl-8-hydroxy-7-(n-propyl)-9H-6-oxo-pyrimido[2,3-f]purine-2,4-dione; and
1,3-Dimethyl-9-(4-fluorobenzyl)-6-hydroxy-7-(3-methyl-2-butenyl)-pyrimido[2,1-f]purine-2,4,8(1H,3H,9H)-trione.

16. The compounds defined in claim 15 in the form of their tautomers, sodium salts or hydrates.

17. A pharmaceutical composition which comprises a compound having structural formula I as defined in claim 1 in combination with a pharmaceutically acceptable carrier.

18. A method of treating inflammation in a mammal which comprises administering the composition defined in claim 17 to said mammal.

* * * * *